Feb. 12, 1963 H. C. SWIM ETAL Plant Pat. 2,226
ROSE PLANT
Filed March 13, 1962
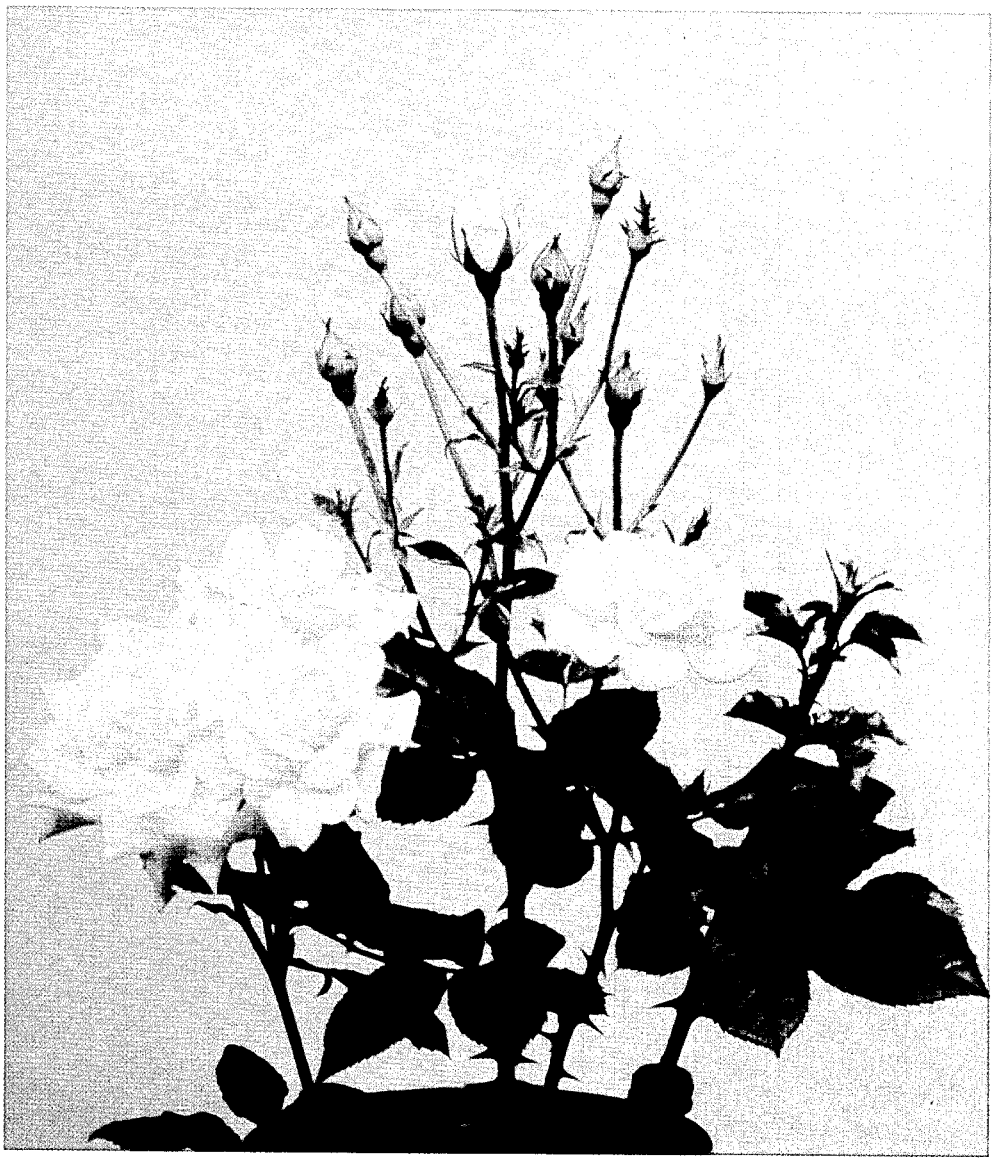
Inventors.
H. C. Swim and
O. L. Weeks
By: Robb & Robb
Attorneys.

United States Patent Office

Plant Pat. 2,226
Patented Feb. 12, 1963

2,226
ROSE PLANT

Herbert C. Swim, Ontario, and O. L. Weeks, Chino, Calif., assignors to Weeks Wholesale Rose Grower, Chino, Calif.

Filed Mar. 13, 1962, Ser. No. 179,502
1 Claim. (Cl. 47—61)

The present invention relates to a new and distinct variety of rose plant of the (floribunda class, which was originated by us by crossing the variety "Yellow Pinocchio" (Plant Patent No. 992) with the variety "Circus" (Plant Patent No. 1,382).

As the result of this breeding, we have produced a new rose variety having the following unique combination of characteristics which are outstanding therein and which distinguish it from its parents, as well as from all other varieties of which we are aware:

(1) A low-growing and compact habit of plant growth;

(2) Large, glossy, dark green leaves;

(3) An abundance of flowers at all times during the blooming period, with relatively large quantities of blooms in the individual sprays, as compared with other varieties of comparable plant size;

(4) An attractive form of both the buds and the open flowers, with the buds and open flowers being of relatively small size in general effect, as compared with other varieties;

(5) Double flower petalage;

(6) A distinctive and attractive deep lemon yellow general color tonality of the flowers; and (7) Good persistence of the yellow flower color throughout the life of the flowers.

In comparison with its seed parent "Yellow Pinocchio," the flowers of our new variety are of a distinctively different color which may be characterized as intense lemon yellow, fading to lemon yellow of a somewhat lesser intensity, as distinguished from the apricot-yellow general color tonality of the flowers of this parent variety which tend to fade to cream color; the new variety is distinctly more upright in its habit of plant growth, as compared with the spreading habit of the parent variety; the new variety is substantially more dwarf in its habit of growth; and the foliage of the new variety is more glossy in contrast to the semi-glossy to non-glossy foliage of "Yellow Pinocchio."

As compared with the pollen parent, "Circus," the plant of our new variety is substantially lower growing in habit; the foliage is substantially more green in color and more glossy in appearance; the flowers are substantially smaller in size, particularly in general effect, and are rarely ever borne singly to the stem as is characteristic of this parent variety, this latter quality resulting in a more effective mass of bloom; and the flowers of the new variety are a uniform shade of yellow color, without other colors, as distinguished from the characteristic blend of red, pink, salmon, orange, and yellow colors of the flowers of "Circus" and which change in emphasis as the buds develop into open flowers.

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Dwarf; bush; outdoor; seedling; for garden decoration.

Class: Floribunda.

Breeding: Seedling.

*Seed parent.*—"Yellow Pinocchio."

*Pollen parent.*—"Circus."

Propagation: Holds its distinguishing characteristics through succeeding propagations by budding.

*Flower*

Locality where grown and observed: Chino, California.

Flowers borne: From 3 to 10 or more to stem; in regular, flat to pyramidal clusters; on stems of medium length and normal strength.

Quantity of bloom: Abundant, both outdoors and in greenhouse.

Continuity: Intermittent throughout growing season.

Fragrance: Slight. Nature—tea.

Bud:

*Peduncle.*—Medium length; medium caliper; erect; stiff; with numerous small red prickles which change to yellow color after the bud matures. Color—medium yellowish green.

*Before calyx breaks.*—Size—medium, for type. Form—short; pointed; with small foliaceous appendages on the surface of the bud; with occasional small and slender foliaceous parts extending beyond the tip of the bud equal to ½ or less of its length. Color—near Brilliant Greenish Yellow, Plate 10Y 9/9.

*As calyx breaks.*—Color—near Vivid Greenish Yellow, Plate 7.5Y 8/12.

*As first petal opens.*—Size—from small to medium, for type. Form—short; from pointed to flat across apex. Color: outside—close to Vivid Yellow, Plate 5Y 8/12, but somewhat more intense yellow; inside—between Vivid Greenish Yellow, Plate 7.5Y 8/12 and Vivid Yellow, Plate 5Y 8/12.

*Opening.*—Opens up well.

Bloom:

*Size (when fully open).*—From small to medium; from 2½ inches to 2¾ inches.

*Petalage.*—Double; from 30 to 35 petals arranged regularly on center blooms to 20 to 25 petals on side blooms of clusters, plus 4 to 5 petaloids.

*Form.*—High-centered at first, but becoming flat with age; petals at first being from flat to rolled outward very slightly and remaining more or less the same shape throughout life of flower.

Petals:

*Texture.*—Medium thick; slightly leathery. Inside—slightly velvety. Outside—satiny.

*Shape.* — Outside — nearly round, but somewhat broader than long; scalloped; with apex having 3 or 4 shallow notches, but sometimes being entire; apex acutely but bluntly pointed. Intermediate—obovate; apex often having 2 very sallow notches. Inside—obovate-truncate; apex usually having 1 notch.

This description of a newly opened flower was made from a rose grown in a greenhouse during the month of February at Chino, California:

*Color.*—Outer petal: outside surface—near Brilliant Greenish Yellow, Plate 7.5Y 9/8; inside surface—near Brilliant Greenish Yellow, Plate 7.5Y 9/8 at base, but outer ⅔ being Brilliant Greenish Yellow, Plate 10Y 9/9. Intermediate petal: outside surface—near Brilliant Yellow Green, Plate 2.5GY 9/8, with Brilliant Greenish Yellow, Plate 7.5Y 9/8; inside surface—Brilliant Greenish Yellow, Plate 10Y 9/9 at base, with outer ⅔ of petal near Brilliant Yellow Green, Plate 2.5GY 9/8. Inner petal: outside surface—near Brilliant Greenish Yellow, Plate 7.5Y 9/8; inside surface—near Brilliant Greenish Yellow, Plate 7.5Y 9/8, with base very slightly more intense.

This description was made from a rose that was open for three (3) days in a greenhouse during the month of February at Chino, California:

*Color.*—Outer petal: outside surface—base Brilliant Greenish Yellow, Plate 7.5Y 9/8, changing progressively toward apex through Brilliant Greenish Yellow, Plate 10Y 9/9 to Brilliant Yellow Green, Plate 2.5GY 9/8, and finally to slightly lighter yellow green at the extreme outer margin; inside surface—base between Vivid Greenish Yellow, Plate 7.5Y 8/12 and Brilliant Greenish Yellow, Plate 7.5Y 9/8, diminishing only slightly progressing toward apex except for about ⅛ inch of margin around the upper half of the petal which is between white and Brilliant Greenish Yellow, Plate 7.5Y 9/8. Inner petal: outside surface—small area at base near Vivid Greenish Yellow, Plate 7.5Y 8/12, with remainder of petal Brilliant Greenish Yellow, Plate 7.5Y 9/8; inside surface—Brilliant Greenish Yellow, Plate 7.5Y 9/8 over major portion of petal, becoming more intense at small area about base and near Vivid Greenish Yellow, Plate 7.5Y 8/12.

*General color effect.*—Newly opened flower—between Vivid Yellow, Plate 5Y 8/12 and Vivid Greenish Yellow, Plate 7.5Y 8/12. 3-days open—between Brilliant Yellow, Plate 5Y 9/9 and Brilliant Greenish Yellow, Plate 7.5Y 9/8.

*Behavior.*—Drop off cleanly, except for petaloids which persist in hot, dry weather; flowers fade with age, but are remarkably uniform in color at any given age.

*Flower longevity.*—Cut roses grown in greenhouse and kept at living-room temperatures—6 days in February.

*Reproductive Organs*

Stamens: From few to medium in number; arranged irregularly about pistils; mixed with petaloids and tucked in calyx.
Filaments: Long; most with anthers. Color—yellow.
Anthers: Small; open at various times. Color—yellow.
Pollen: Sparse. Color—from gold to yellow.
Pistils: Few.
Styles: Uneven; from short to medium length; from thin to medium caliper; loosely bunched.
Stigma: Color—Whitish yellow.
Ovaries: All enclosed in calyx.
Hips: Globular; smooth; walls thick and fleshy for size; relatively small for class. Color—yellow and russet when mature.
Sepals: Permanent; short; recurved.
Seeds: Few; small.

*Plant*

Foliage:

*Leaves.*—Compound of 3 to 5 leaflets; from normal quantity to abundant; large size; moderately heavy; leathery; glossy.

*Leaflets.*—Shape—ovate, with apex acute-mucronate. Base—nearly round. Margin—simply serrate and relatively flat.

*Color.*—Mature: upper surface—very dark green; under surface—normal grey-green. Young: upper surface—nearly Dark Greenish Yellow, Plate 10Y 6/7, with serrations bronze-red; under surface—grey-green, with bronze-red overlay.

*Rachis (the supporting stem of the compound leaf).*—Medium weight and caliper. Upper side—smooth; grooved; with ridges sparsely lined with stipitate glands. Under side—smooth, except for 2 or 3 prickles.

*Stipules.*—Moderately short; narrow; with short points turning out at an angle of from 45° to 90°.

*Disease resistance.*—Good and better than average resistance to mildew, with average or medium susceptibility to rose rust under field conditions, all as compared with other varieties grown under comparable conditions at Chino, California.

Growth:

*Habit.*—Dwarf; bushy; upright; much-branched.

*Growth.*—Moderately free.

*Canes.*—Moderately light.

*Main stems.*—Color—from light grey-green to yellow-green. Large prickles—many; medium length; straight; with short, broad base; color—light brown. Small prickles—few; color—light brown. Hairs—none.

*Branches.*—Color—bright yellow-green. Large prickles—many; medium length; straight; with short base of medium width; color—dark brown. Small prickles—few; color—dark brown. Hairs—none.

*New shoots.*—Color—bright yellow-green. Large prickles—many; from medium length to long; straight; with short base of medium width; color—bronze-red. Small prickles—few; color—reddish bronze. Hairs—none.

We claim:

A new and distinct variety of rose plant of the floribunda class, substantially as herein shown and described, characterized particularly as to novelty by the unique combination of a low-growing and compact habit of plant growth, large, glossy, dark green leaves, the presence of an abundance of flowers at any given period of bloom, with relatively large quantities of blooms in the individual sprays, an attractive form of the buds and open flowers, said buds and open flowers being of relatively small size in general effect, double petalage of the flowers, a distinctive and attractive deep lemon yellow general color tonality of the flowers, and good persistence of the yellow flower color throughout the life of the flowers.

No references cited.